(12) United States Patent
Hefetz et al.

(10) Patent No.: US 9,182,507 B2
(45) Date of Patent: Nov. 10, 2015

(54) IMAGING SYSTEM USING HIGH AND LOW ENERGY COLLIMATION

(71) Applicant: General Electric Company, Schenectady, NY (US)

(72) Inventors: Yaron Hefetz, Kibbutz Alonim (IL); Jean-Paul Bouhnik, Zichron Yaacov (IL); Arie Eshco, Haifa (IL)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/501,337

(22) Filed: Sep. 30, 2014

(65) Prior Publication Data

US 2015/0177392 A1    Jun. 25, 2015

Related U.S. Application Data

(63) Continuation-in-part of application No. 14/135,751, filed on Dec. 20, 2013.

(51) Int. Cl.

| | |
|---|---|
| *G01T 1/10* | (2006.01) |
| *G01T 1/29* | (2006.01) |
| *G01T 1/161* | (2006.01) |
| *G01T 1/24* | (2006.01) |
| *A61B 6/03* | (2006.01) |
| *A61B 6/00* | (2006.01) |
| *G06T 11/00* | (2006.01) |

(52) U.S. Cl.
CPC ............... *G01T 1/2985* (2013.01); *A61B 6/037* (2013.01); *A61B 6/4258* (2013.01); *A61B 6/4266* (2013.01); *G01T 1/161* (2013.01); *G01T 1/249* (2013.01); *G06T 11/005* (2013.01); *A61B 6/503* (2013.01); *A61B 6/545* (2013.01); *A61B 6/547* (2013.01); *G06T 2207/10108* (2013.01); *G06T 2207/20172* (2013.01)

(58) Field of Classification Search
CPC ............................ G01T 1/2985; G01T 1/1648
USPC ........................................................ 250/362
See application file for complete search history.

(56) References Cited

U.S. PATENT DOCUMENTS

| | | | | |
|---|---|---|---|---|
| 3,774,031 | A * | 11/1973 | Mallard et al. ............. | 250/503.1 |
| 5,436,958 | A | 7/1995 | Taylor | |
| 6,271,524 | B1 | 8/2001 | Wainer et al. | |
| 7,601,966 | B2 * | 10/2009 | Ben-Haim et al. ............ | 250/394 |
| 2014/0343412 | A1 * | 11/2014 | Wieczorek et al. ........... | 600/425 |

\* cited by examiner

*Primary Examiner* — Kiho Kim
(74) *Attorney, Agent, or Firm* — Lucas Davine

(57) ABSTRACT

A customizable and upgradable imaging system is provided. Imaging detector columns are installed in a gantry to receive imaging information about a subject. Imaging detector columns can extend and retract radially as well as be rotated orbitally around the gantry. The system can provide detector columns that include both high and low energy collimation. The detector columns may also use side shielding and adaptively disable detector elements based on emission information and shielding information. This system can be a Nuclear Medicine (NM) imaging system to acquire Single Photon Emission Computed Tomography (SPECT) image information.

20 Claims, 16 Drawing Sheets

IMAGING SYSTEM USING HIGH AND LOW ENERGY COLLIMATION

PRIORITY AND REFERENCE TO RELATED APPLICATIONS

This application is a continuation-in-part of U.S. patent application Ser. No. 14/135,751, entitled "IMAGING SYSTEM USING INDEPENDENTLY CONTROLLABLE DETECTORS", filed Dec. 20, 2013, the disclosure of which is incorporated by reference herein as if set forth in its entirety.

BACKGROUND

The subject matter disclosed herein relates generally to medical imaging systems, and more particularly, to Nuclear Medicine (NM) imaging systems which can be Single Photon Emission Computed Tomography (SPECT) imaging systems.

In NM imaging, such as SPECT imaging, radiopharmaceuticals are administered internally to a patient. Radiopharmaceuticals may also be referred to as tracers. Detectors (e.g., gamma cameras), typically installed on a gantry, capture the radiation emitted by the radiopharmaceuticals and this radiation information is used by computer processors running image reconstruction algorithms to form images. The NM images primarily show physiological function of, for example, the patient or a portion of the patient being imaged.

Conventional SPECT imaging systems include one or two gamma cameras mounted to a single gantry. These systems are generally not physically reconfigurable and can only handle one radiation energy level at a time. Additionally, specific collimation may be provided, which typically limits the application of the scanner to a particular type of scan, such as whole body bone exams, cardiac exams, etc. Thus, conventional SPECT imaging systems have limitations in design and/or operational characteristics. Moreover, there is limited flexibility in these imaging systems, especially when it comes to situations where both high and low energies need to be detected by the gamma cameras. There is a need for flexibility of an imaging system to be customizable based on specific patient need, scan type, organ scanned, and operator cost constraints.

BRIEF DESCRIPTION

In accordance with an embodiment, an imaging system is provided, comprising: a gantry with a bore therethrough; a plurality of imaging detector columns attached to the gantry, extending inside the gantry bore; a plurality of detector elements installed in each detector column; wherein, for each detector column, a portion of the plurality of detector elements are each attached to a low energy collimator and a remaining portion of the plurality of detector elements are each attached to a high energy collimator. The system can further include computer processing circuitry to develop an image acquisition scenario based system installation information and a requested imaging operation to be performed by the plurality of detector columns; configure a physical position of a least one detector column based on the developed image acquisition scenario; acquire image information from at least one detector element; reconstruct image information into medical images; and send said medical images to a display screen or a computer memory.

Further, in accordance with an embodiment, the at least one of the plurality of detector columns are configured to acquire Single Photon Emission Computed Tomography (SPECT) data, the low energy collimator can be a thin-septa collimator, and the high energy collimator can be a thick-septa collimator or a pinhole collimator.

In some embodiments, each detector column has the same configuration, wherein: the plurality of detector elements attached to a low energy collimator are adjacent to one another and set towards one axial side of the detector column; and the remaining portion of the plurality of detector elements attached to a high energy collimator are adjacent to one another and set towards the opposite axial side of the detector column. Detector columns can simultaneously detects emissions from multiple isotopes inside an imaging subject in some embodiments. Detector columns can further include shielding elements attached to at least two sides of a detector column to prevent radiation from reaching said detector elements from a side angle, and if a detector column detects received radiation from a side comprising a shield element, the system disables at least one detector element near to said side of the detector column.

In accordance with an embodiment, an image detector unit is provided, including a detector head comprising a plurality of detector elements; an arm for connecting the detector head with a support structure; a sweep motor for altering an angle of the detector head; and wherein, at least a portion of the plurality of detector elements are each attached to a low energy collimator and the remaining portion of the plurality of detector elements are each attached to a high energy collimator. The detector head can further include shielding elements attached to at least two sides of the detector head to prevent radiation from reaching said detector elements from a side angle; and wherein if a detector unit detects received radiation above a preset threshold from a side comprising a shield element, the detector unit disables at least one detector element near to said side of the detector unit.

In accordance with an embodiment of the detector unit, the detector elements are arranged in a row; and detector elements attached to a high energy collimator and detector elements attached to a low energy collimator are positioned in a staggered manner.

In accordance with an embodiment, an imaging system is provided, including a plurality of image detectors attached to the gantry, extending inside the gantry bore; wherein at least one image detector includes only high energy collimation and at least one image detector includes only low energy collimation. The system can further include an annular rotary member attached to the gantry, wherein the plurality of image detectors are attached to the rotary member such that rotary member rotation causes the image detectors to orbit around the center of the bore; wherein if a high energy medical scan is initiated in the system, the rotary member rotates the at least one image detector with high energy collimation near to a region of interest; and wherein if a low energy medical scan is initiated in the system, the rotary member rotates at least one image detector with low energy collimation near to a region of interest.

In accordance with an embodiment, an imaging method in a medical imaging system with a gantry and a plurality of image detectors is provided that includes determining installation information of the system, wherein installation information includes high energy collimator configuration and low energy collimator configuration for each image detector; acquiring SPECT data simultaneously from a plurality of isotopes inside an imaging subject, wherein at least one isotope emits high energy radiation and at least one isotope emits low energy radiation; adjusting, based on said installation information, a detector head angle of at least one image detector, continuing the data acquisition from another imaging angle. Further, each image detector includes a plurality of detector elements; high energy collimator configuration information includes the specific detector elements, for each image detector, that are attached to a pinhole collimator or thick septa collimator; and low energy collimator configuration information includes the specific detector elements, for each image detector, that are attached to a thin septa collimator.

A customizable and upgradable imaging system is provided. Imaging detector columns are installed in a gantry to receive imaging information about a subject. Imaging detector columns can extend and retract radially as well as be rotated orbitally around the gantry. The system can provide detector columns that include both high and low energy collimation. The detector columns may also use side shielding and adaptively disable detector elements based on emission information and shielding information. This system can be a Nuclear Medicine imaging system to acquire Single Photon Emission Computed Tomography image information.

DETAILED DESCRIPTION

Figure 1:
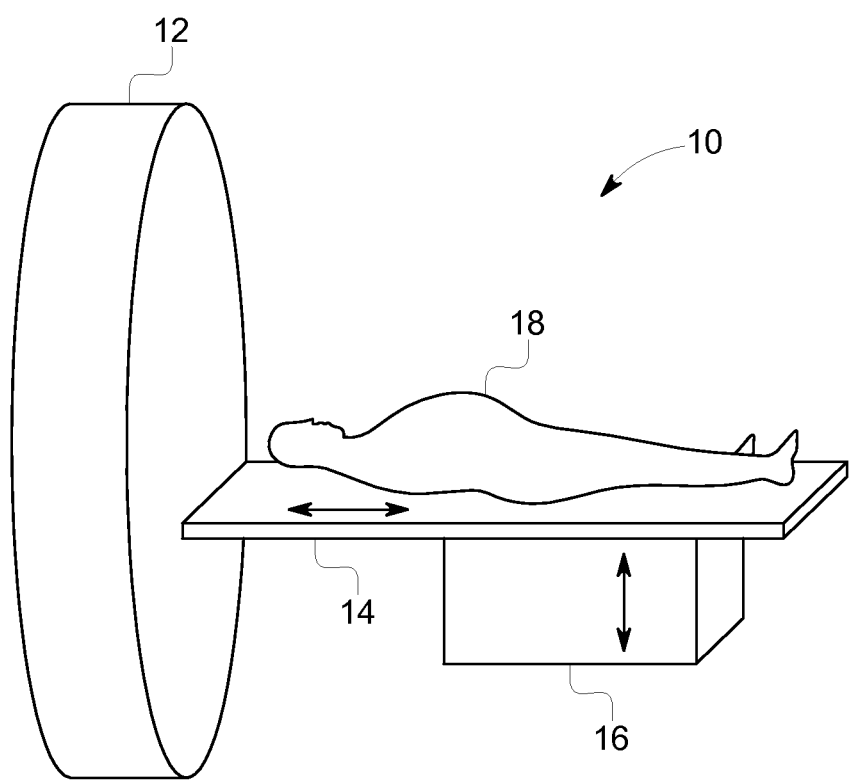
FIG. 1 is a perspective view of a medical imaging system, according to an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a medical imaging system, and in particular, a Nuclear Medicine (NM) imaging system having a gantry with a plurality of imaging detectors mounted thereto. For example, in various embodiments of an NM imaging system, a Single Photon Emission Computed Tomography (SPECT) imaging scanner is provided that includes a plurality of detector columns with a combination of different types of detector elements that acquire SPECT image information. The various embodiments may include detectors formed from different materials, having different configurations or arrangements, having different collimation, etc. The system may be configured to perform single isotope or multi-isotope imaging. The system may be configured to detect both high and low energy emissions. Low energy emissions are generally below 159 keV (kilo-electronvolts). High energy emissions are generally at or above 159 keV.

It should be noted that although the various embodiments are described in connection with a particular NM imaging system, such as a SPECT detector system, the various embodiments may be implemented in connection with other imaging systems, such as a Positron Emission Tomography (PET) imaging system. Additionally, the imaging system may be used to image different objects, including objects other than people.

FIG. 1 is a perspective view of medical imaging system 10, according to an embodiment. A subject 18 can be a human patient in an embodiment. The subject 18 can be placed on a pallet 14 that can move a subject horizontally for locating the subject in the most advantageous imaging position. Bed mechanism 16 can raise and lower pallet 14 vertically for locating the subject in the most advantageous imaging position. Gantry 12, or support structure, is shown as circular in one embodiment. In other embodiments gantry 12 may be of any shape such as square, oval, "C" shape, or hexagonal.

Figure 2:
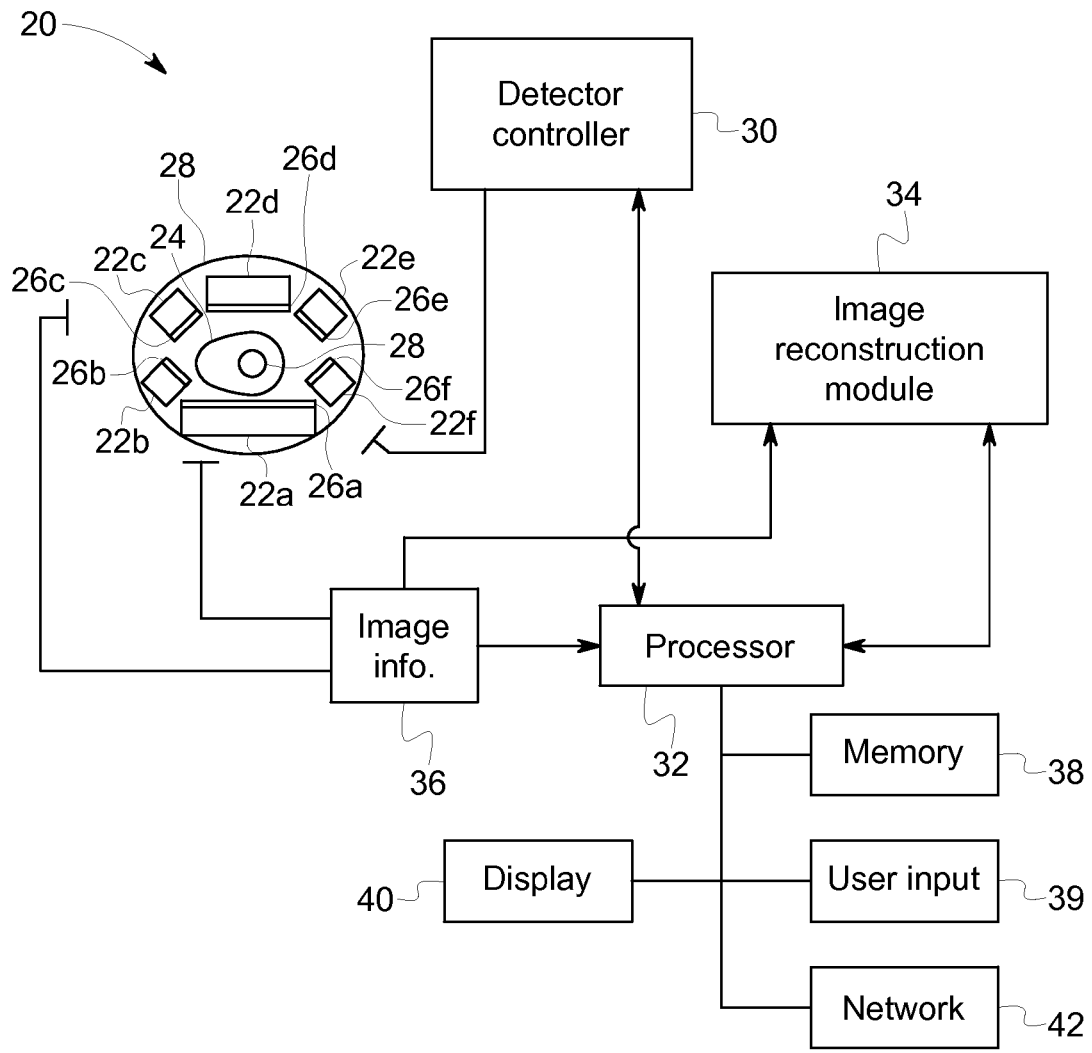
FIG. 2 is a schematic block diagram illustrating a medical imaging system, according to an embodiment.

FIG. 2 shows a medical imaging system, according to an embodiment. Medical imaging system 20 may be provided having a plurality of NM cameras configured as SPECT detector columns 22a-22f. It should be noted that the various embodiments are not limited to medical imaging system 20 having six detector columns 22 as shown or to the sizes or shapes of the illustrated detector columns 22. For example, medical imaging system 20 may include more or less detector columns 22 having different shapes and/or sizes, or formed from different materials. The medical imaging system 20 in various embodiments is configured as a hybrid SPECT system having a plurality of detector columns 22, wherein at least two of the detectors are formed from different materials, have different configurations or arrangements, have different collimation, or are otherwise different. Detector columns can be called detector units in some embodiments.

In operation, a subject, such as a patient 24, is positioned in proximity to the one or more of the detector columns 22 for imaging. Imaging system 20 can then re-adjust detector columns 22 further from or closer to patient 24 or patient area of interest as needed, which is heart 28 in an example embodiment. Imaging of patient 24 is performed by one or more detector columns 22. The imaging by each of the detector columns 22 may be performed simultaneously, concurrently, or sequentially.

The position of detector columns 22 may be varied, including the relative position between detector columns 22, tilt, angle, swivel, etc. of the detector columns 22. Additionally, each of the detector columns 22 may have a corresponding collimator 26a-26f mounted or coupled thereto. Collimators 26a-26f likewise may be of different types. One or more detector columns 22 may be coupled to a different type of collimator 26 (e.g., parallel hole, pin-hole, fan-beam, cone-beam, etc.). Accordingly, in various embodiments, detector column 22 wholly includes collimator 26. As further discussed below, a detector column 22 may include multiple types of collimators in its detector head to provide for both high and low energy radiation detection.

Detector columns 22 may include single crystal, or multi-crystal, solid state, detectors or pixelated detectors or scintillator based detectors that are configured to acquire SPECT image data. For example, detector columns 22 may have detector elements formed from different materials, such as semiconductor materials, including Cadmium Zinc Telluride (CdZnTe), often referred to as CZT, Cadmium Telluride (CdTe), and Silicon (Si), among others, or non-semiconductor scintillator materials such as different types of crystal scintillators, for example, Sodium Iodide (NaI), Bismuth Germanate (BGO), Cerium-doped Lutetium Yttrium Orthosilicate (LYSO), Gadolinium Oxyorthosilicate (GSO), Cesium Iodide (CsI), Lanthanum(III) bromide (LaBr$_3$), among others. Additionally suitable components may be provided. For example, detector columns 22 may be coupled to photosensors, such as an array of Photo-Multiplier Tubes (PMTs), an Avalanche Photodiode Detector (AFD), silicon photomultipliers (SiPM), etc. Detector elements may be solid state pixelated detectors.

Imaging system 20 can also include a detector controller 30 that operates to control the movement of detector columns 22 and/or collimators 26. For example, detector controller 30 may control movement of detector columns 22, such as to rotate or orbit detector columns 22 around patient 24, and which may also include moving detector columns 22 closer or farther from the patient 24 and pivoting/swiveling detector columns 22, such that more localized movements or motions are provided. Detector controller 30 additionally may control the orbital rotation of detector columns 22 around the edges of the gantry bore, such that detector columns 22 are at a new angle to patient 24 than previously. This may be done by an annular rotary member installed in the gantry. Detector controller 30 may also optionally control movement of collimators 26, such as independently of detector columns 22. It should be noted that one or more detector columns 22 and/or collimators 26 may move during imaging operation, move prior to, but remain stationary during imaging operation, or may remain in a fixed positioned or orientation. In various embodiments, detector controller 30 may be a single unit controlling movement of both detector columns 22 and collimators 26, may be separate units, or may be a single unit controlling only operation of detector columns 22 or may be a single unit controlling only operation of collimators 26. Imaging system 20 also includes an image reconstruction module 34 configured to generate images from acquired image information 36 received from detector columns 22. For example, image reconstruction module 34 may operate using NM image reconstruction techniques to generate SPECT images of patient 24, which may include an object of interest, such as heart 28 of the patient. The image reconstruction techniques may be determined based on the installation status of detector column 22 acquiring image information 36 and sending to image reconstruction module 34 and/or processor 32. Variations and modifications to the various embodiments are contemplated. For example, in a multi-headed system, namely a system having two or more detector columns 22, each detector column 22 may be formed from different materials and have different collimators 26. Accordingly, in at least one embodiment, one detector combination may be configured to obtain information for an entire field of view (FOV), such as the entire spine, while another detector combination is configured to focus on a smaller region of interest (ROI) to provide higher quality information (e.g., more accurate photon counting). Additionally, information acquired by one detector combination may be used to adjust the position, orientation, etc. of at least one other detector combination during imaging.

Image reconstruction module 34 may be implemented in connection with or on a detector controller 30 and/or processor 32 that is coupled to the imaging system 20. Optionally, image reconstruction module 34 may be implemented as a module or device that is coupled to or installed in detector controller 30 and/or processor 32. Each processing module may be a separate hardware module or software module, or combined together into one chip or module in various embodiments.

The image information 36 received by processor 32 and/or image reconstruction module 34 may be stored for a short term (e.g., during processing) or for a long term (e.g., for later offline retrieval) in a memory 38. Memory 38 may be any type of data storage device, which may also store databases of information. Memory 38 may be separate from or form part of processor 32. A user input 39, which may include a user interface selection device, such as a computer mouse, trackball and/or keyboard is also provided to receive a user input. The user input may direct processor 32 to send a detector control signal to detector controller 30 for alteration of the detector column 22 arrangement in the gantry bore. Optionally, user input 39 may be considered by processor 32 as a suggestion and processor 32 may choose to not execute the suggestion based on criteria.

Thus, during operation, the output from detector columns 22, which may include image information 36, such as projection data from a plurality of detector/gantry angles is transmitted to processor 32 and image reconstruction module 34 for reconstruction and formation of one or more images. The reconstructed images and other user output can be transmitted to a display 40 such as a computer monitor or printer output. The reconstructed images and other user output can also be transmitted to a remote computing device via network 42.

Different combinations and variations of detector columns 22 and/or collimators 26 will now be described. It should be noted that the various embodiments are not limited to a particular detector, collimator, or detector combination, but may include any imaging system having a plurality of different types of detector columns 22 and/or collimators 26, for example, having at least two detector columns 22 of a different type or design. Additionally, the number of detector columns 22 and the arrangement thereof may be varied as desired or needed, for example, based on the type of imaging to be performed or the type of image information to be acquired. Accordingly, various embodiments include the imaging system 20 having a plurality of detector columns 22, wherein at least two of the detector columns 22 are different and are configured to perform imaging of the patient 24 (or other object).

For example, in one embodiment, illustrated in FIG. 2, a configuration is provided having one detector column 22a formed from one material and the remaining detector columns 22b-22l formed from a different material. In the illustrated embodiment, the detector column 22a is formed from a NaI material and the remaining detector columns 22b-22l are formed from a CZT material. Accordingly, in this configuration, a single NaI detector column 22a and a plurality of CZT detector columns 22b-22l are provided. The detector columns 22a-22l may be sized and shaped the same or differently. For example, in the embodiment illustrated in FIG. 2, the NaI detector column 22a is larger than each of the CZT detector columns 22b-22l, such that the NaI detector column 22a can image the entire patient 24 and the CZT detector columns 22b-22l are configured to focus on a portion of the patient 24, such as the heart 28. In this embodiment, one or more of the CZT detector columns 22b-22l may be positioned and oriented at different angles or tilted differently to provide focused imaging. However, one or more of the CZT detector columns 22b-22l may be angled or tilted the same. In the embodiment of FIG. 2, the CZT detector columns 22b-22l are angled such that together the CZT detector columns 22b-22l focus on the overall body of patient 24, instead of on a particular ROI, such as heart 28. Thus, one or more detector columns 22 may be arranged and configured to cover an entire FOV of an imaged, while one or more other detectors are arranged and configured to cover a focused FOV within the object.

It should be noted that as used herein, a set of detectors is generally referred to as detector columns 22 and a set of collimators is generally referred to as the collimators 26. Moreover, the use of letter designations after the numeral designation for detector columns 22 and collimators 26 are used for ease of illustration and do not necessarily represent the same detector columns 22 or collimators 26 in the various embodiments or figures. Thus, the letter designation represents the relative positioning of the detector columns 22 or collimators 26 and not necessarily the type or kind of detector. Additionally, the size and shape of detector columns 22 may be varied as desired or needed.

In FIG. 2, collimators 26a-26l may be the same or may be different. For example, collimator 26a may be of a first type, such as a parallel hole collimator (with thick septa or thin septa), while collimators 26b-26l may have different types (e.g., converging, diverging, or pinhole) based on a desired or required sensitivity or resolution, as well as the position and orientation of detector column 22 on which collimator 26 is coupled. Thus, collimators 26 may be of any type. A thin septa collimator generally is one that provides gamma ray penetration greater than 1.5% at 140 keV. A thick septa collimator generally is one that provides gamma ray penetration of less than 1.5% at 140 keV.

Figure 3:
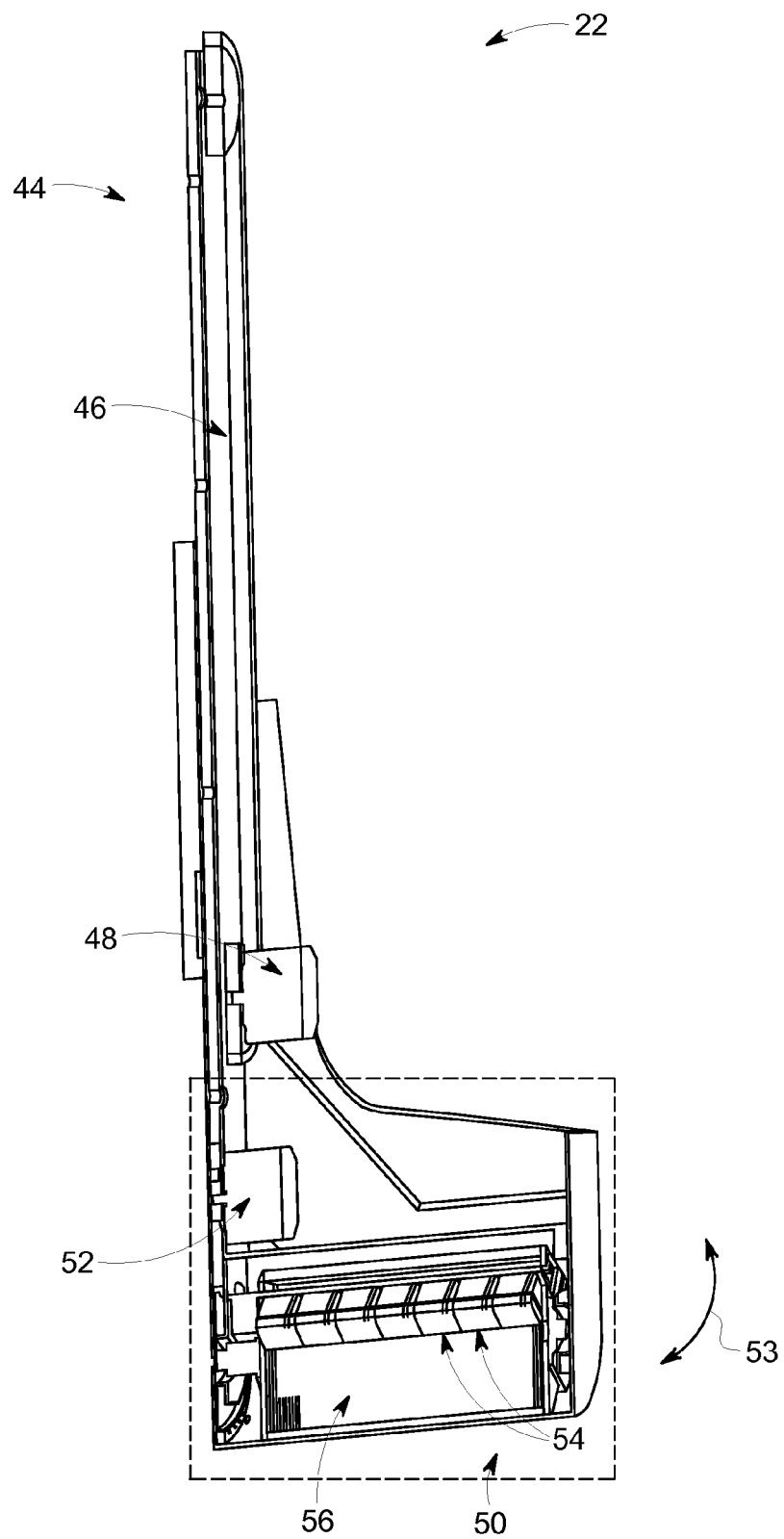
FIG. 3 is a detailed view of a detector column design, according to an embodiment.

FIG. 3 shows a detailed implementation of detector column 22, according to an embodiment. Column arm 44 attaches to a gantry and provides support for and includes a radial motion rail 46, radial motion motor 48, and detector head 50. The radial motion motor 48 controls the movement of detector head 50 by extending or retracting the detector head 50 along radial motion rail 46. This provides customizability and flexibility to the imaging system. The detector column can include telescopic covers that allow it to extend and contract as it moves radially in and out.

Detector head 50 includes a sweep motor 52, detector elements 54, and collimator 56. Detector elements 54 can be CZT modules or other detector element modules discussed throughout for detecting imaging data. Sweep motor 52 controls the rotation angle of detector head 50 in relation to arm 44. The sweep pivoting axis 53 shows the rotation angle axis of detector head 50. Detector controller 30 can provide instruction and control to either or both of radial motion motor 48 and sweep motor 52. Thus, each detector column 22 is independently controllable in the radial location as well as the angle of tilt of detector head 50. Radial motion motor 48 and sweep motor 52 can be two separate motors as shown in the embodiment of FIG. 3. Alternatively, the functionality of the two motors may be provided by one motor.

Figure 4:
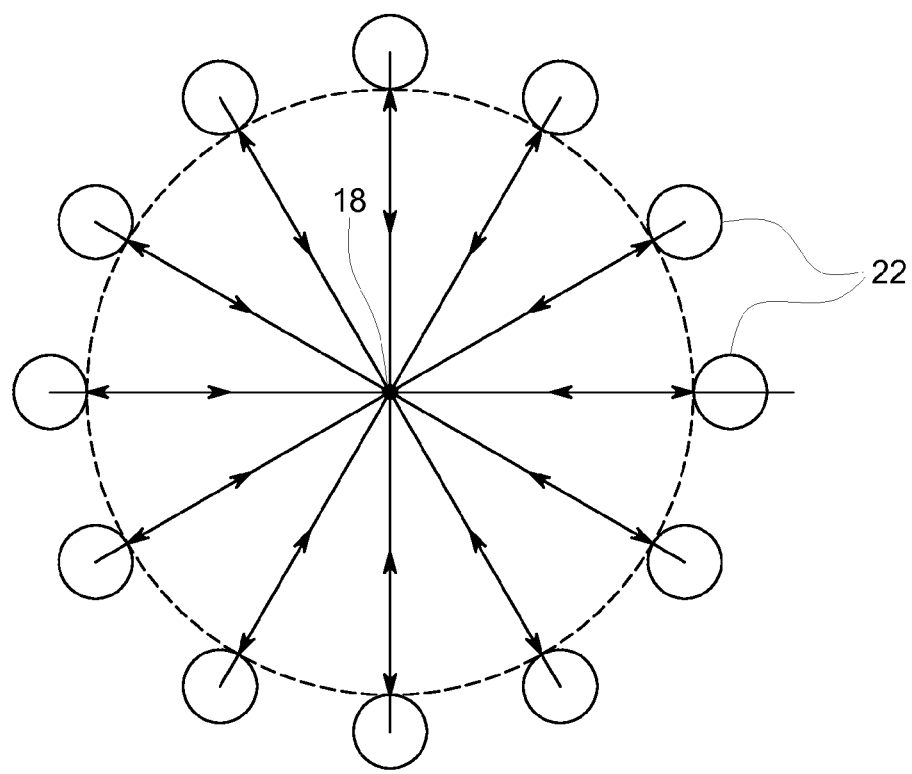
FIG. 4 is a radial construction of an imaging system, according to an embodiment.

FIG. 4 is a radial construction of an imaging system, according to an embodiment. Twelve detector columns 22 are placed at a consistent angle, thirty degrees in this example, from each other along the inside of a gantry bore. Thus, detector columns 22 are uniformly distributed in this example. Each detector column 22 is movable along a radial axis. This allows detector columns 22 to be closer or further from a subject 18 for imaging. The circles in the figure depict the location of detector head 50 of detector column 22. The detector columns are shown along the dotted line as their outer limit position in this view of one embodiment. The dual head radial arrows depict the in-out direction of motion of the detector columns 22.

Figure 5:
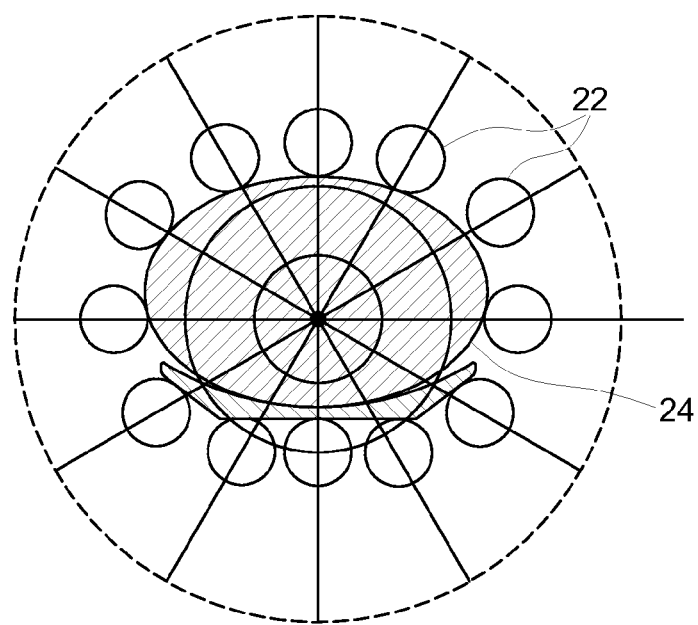
FIG. 5 is a diagram of the detector columns controlled to move to different points of their radial axis to best scan the specific shape of a subject, according to an embodiment.

FIG. 5 is a radial construction of an imaging system where twelve detector columns 22 have their heads placed at a consistent angle and have been moved radially inward to be in positions close to a patient 24, according to an embodiment. As FIG. 5 shows, some of the detector heads are further towards the center of their radial axis than others. This allows for high-quality imaging results with varied-sized objects.

Figure 6:
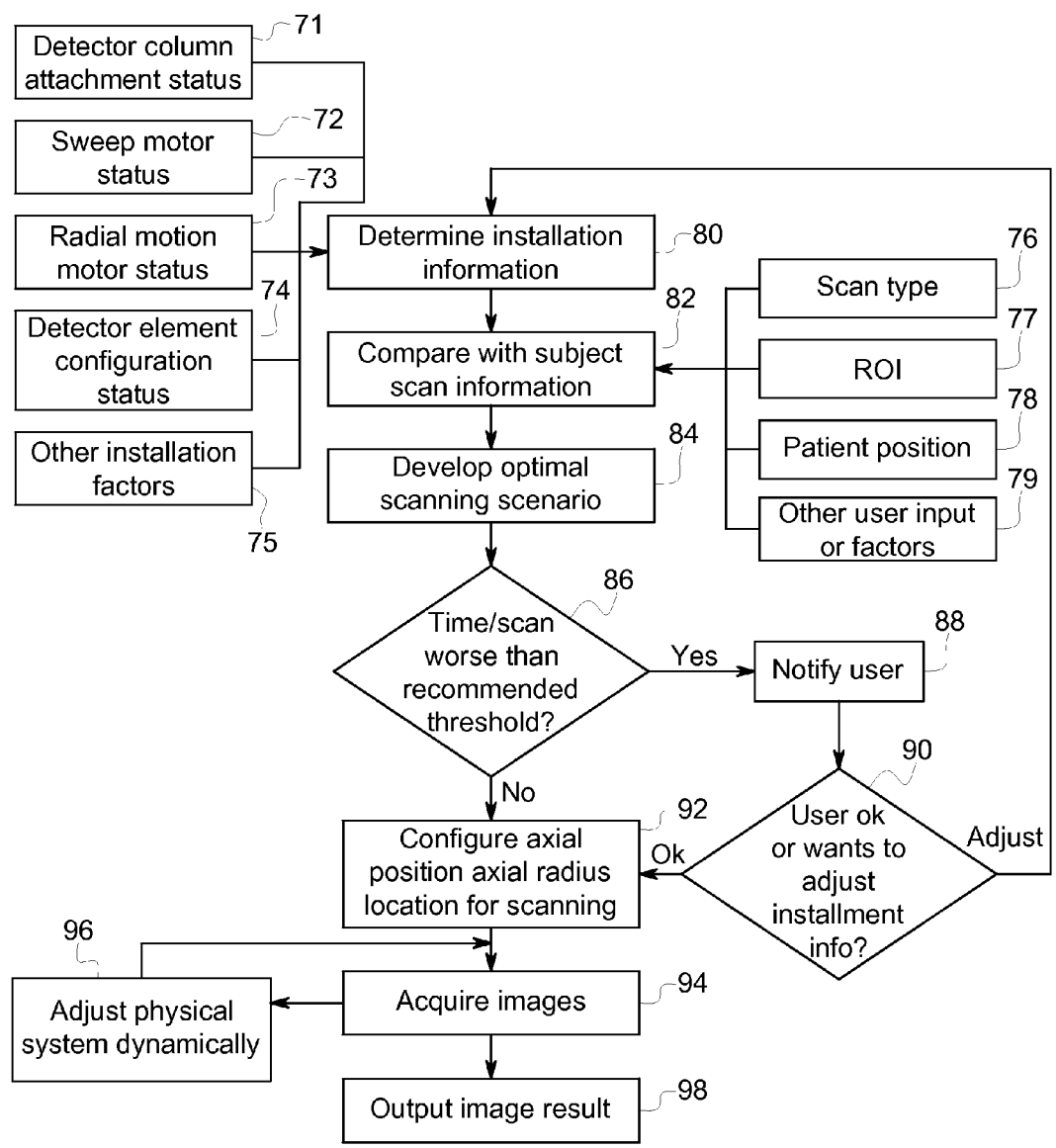
FIG. 6 is a flowchart depicting a method of operation, according to an embodiment.

FIG. 6 is a flowchart depicting a method of operation, according to an embodiment. The steps as shown do not necessarily have to flow in the order as listed, but are shown in this order just as an example.

In step 80, the system determines installation information. This helps determine what operations and features are available in the system. Installation information, in some embodiments, can included detector column attachment status 71 which indicates in which receiver locations detector columns 22 are installed and in which receiver locations detector columns 22 are not installed. This can tell the system both how far each detector unit can be extended radially as well as how much orbital movement of the detector units will need to occur during operation. Installation information can further include sweep motor status 72. This status can indicate whether each detector column 22 has a sweep motor 52 for head rotation capability, whether the sweep motor 52 is operable, and its range of motion (in circumstances when some detector heads 50 are configured to rotate further than others), or not responding. Installation information can further include radial motion motor status 73. This status can indicate whether each detector column 22 has a radial motion motor 48, its radial motion distance, radial location status, and whether or not the motor is currently operable. Installation information can further include detector element configuration status 74. This status can indicate the specific locations where detector elements 54 are installed and specific locations where detector elements 54 could be installed but are not installed. This status can also indicate what materials are being used to detect the imaging data. This status can also indicate what type of detector material is used, for example: thin (for example, 5 mm in an embodiment) CZT crystal or thick (for example, 7 mm in an embodiment) CZT crystal. Thick CZT crystals can be better suitable for high energies and are preferably used whenever high energy collimators (such as thick septa or pinholes) are used. However, thick crystal may be used with low energy collimators. Each detector column or detector element could have different scintillator or semi-conductor materials installed. Detector element configuration status 74 can also indicate what collimator 56 (or collimators) structure is used in the detector head. As mentioned above, different collimators 56 can be utilized in different detector heads 50. Installation information can further include other installation factors 75, including gantry rotation ability. This is an indication of how many degrees of rotation (or how many 'steps') the gantry can rotate detector columns around the orbit of the gantry. Installation information can further include other installation factors 75 such as the room the imaging system is set up in, factors input by a user, safety information, and other types of information about the installation of the system overall, not just the installation status of the components in the imaging system. For example, many SPECT systems are placed in SPECT/CT (computed tomography) combined system, and the system may also acquire information related to what CT setup is installed.

Installation information can be dynamically updated by processor 32 or detector controller 30 based on information from installation verification elements in receiver locations, and stored in memory 38 in one embodiment. Receiver locations are spots on the gantry where detector columns can be installed. Thus, the verification elements detect installation status of detector columns. Installation verification elements can be any sort of switch, button, sensor, or other device that detects the presence of hardware installed or not installed in the system. Installation verification elements of receiver locations are one way that the system can detect and update installation information. Installation information in one embodiment relates to the detector column arm 44 being physically attached to gantry 62. Further, installation information in another embodiment detects both physical attachment plus a fully functioning arm. In this embodiment, if any of the radial motion motor 48, sweep motor 52, and/or detector elements 54 are inoperable, even though the detector column 22 is attached to the gantry 12, the installation information could indicate the detector column as uninstalled and/or inoperable. Installation information can also indicate the population of specific detector elements 54, as further discussed below.

Installation information is also called configuration information in some embodiments. This is because installation information gives information related to the current hardware configuration in the imaging system, and can be dynamically updated. Thus, installation information, sometimes called configuration information, is not just the initial setup information of the system when delivered to a customer, but is information dynamically updated based on many hardware factors throughout the lifetime of the system.

In step 82, the system compares the installation information with what a specific imaging scan will be and subject information. The imaging scan type information 76 (such as CT, SPECT, PET, MRI, or can be related to the specific radiopharmaceutical being used or the type of medical examination performed) can be considered. The region of interest information 77 (such as cardiac, brain, thyroid) can be considered. Additionally, the type of radiopharmaceutical being used influences the gamma energy range. Since different detectors (or columns) may be optimized for different energies, step 84 may be greatly affected by the energy range. The patient position information 78 on the pallet or bed can be considered. The subject size, age, gender, weight, and other medical characteristics (patient body-type information or patient medical information or subject specific information) can impact the process relating to other user input factors 79. The imaging scan is generally a NM imaging scan based on acquiring SPECT data, but the system could be used in other scanning arrangements for other types of imaging information.

In step 84, the imaging system 20 develops an optimal scanning scenario based on the installation information compared with the subject scan information. For example, if the scan is a cardiac scan and the subject patient is small, a selected scenario would set the radial extension of the arms to high and the detector columns will be recommended to move orbitally towards the sides of the gantry closest to the heart. If the angle of the subject is difficult, the scenario may include rotating some of the detector heads 50 to be more accurately aligned towards the subject. Since different detector columns may be optimized for different energies, positioning of detector columns optimized for the energy range in used in critical positions in respect to the organ of interest is given higher priority than the positioning of detectors not optimized for the energy range in used during planning the optimal scanning scenario.

In step 86, the system makes a decision whether the scanning scenario can be performed within a threshold time. This can also be called a total imaging operation time prediction. This determination considers how long it will take the system to do the full requested imaging based on the imaging time plus system rearrangement time when it is being reconfigured to get additional scanning data. The threshold can be based on an 'acceptable' time set by a user, a subject patient preferred time, a normalized time compared to most scans of the type being done, and/or related to a threshold of safety. The total imaging operation time prediction also considers how long it may take to adjust the patient and how long it takes to adjust the detector columns, detector heads, and/or detector elements. If the time to complete the optimal scanning scenario is higher than a threshold, the system goes to step 88, otherwise continuing on to step 86.

In step 88, a user is notified that the current installation setup of the system may not be able to complete the requested scan in a threshold time. A list of options may also be presented to the user relating to steps the user can take to mitigate any issues or override the issue.

In step 90, the user decides whether to alter the installation arrangement/setting of the system or not. The user can input a response back to the system of their intention. The user can adjust the system manually, in some respects, and automatically through computer control in other respect. If a user adjusts the system, thus altering installation information, the method returns to step 80 to re-evaluate the installation information. If the user is OK with the time threshold being met or exceeded, the system can proceed to step 92.

In step 92, the system performs the physical modifications recommended in the optimal scanning scenario. This can include configuring the detector column axial position around the gantry orbit, the axial radius location for scanning (how far or close to patient along the axial radius), detector head angle as controlled by the sweep motor, and other physical adjustments discussed throughout.

In step 94, the subject is in the system and the images are acquired. If multiple physical positions of detector columns 22, detector heads 50, and/or detector elements 54 are needed, the system adjusts them during the imaging operation at step 96. This is an example of dynamically adjusting of the physical system.

In step 98, the final requested image data is output. A reconstruction algorithm may be applied after the image data acquisition or proactively during the image data acquisition. The output can be to a display, network connected computing device, a printer, picture archive and communication system (PACS) or other output location.

Because the imaging system of at least one embodiment can start with limited installation equipment, the system can perform lower-cost imaging, while also providing upgradability. For example, if a hospital has a small budget and only will perform cardiac scans, they can purchase a system with detector columns setup best for cardiac and not including additional detector columns that can add additional cost. The hospital can still do other types of scans, but will have to wait longer for the system to re-adjust to different image scan scenarios to handle the different scan type. This can add time and sometimes provide a lower quality image than a fully populated or otherwise customized system. The hospital can upgrade and purchase more detector columns, or detector columns with the optional detector head sweep feature, or detector columns with the optional detector radius extension feature, or detector columns with multiple types of image acquisition materials and install them into the system for improved performance. This also applies to detector elements. Detector elements are a driver of cost as well. So a hospital, for example, could purchase one with lower detector element count and upgrade later.

Figure 7:
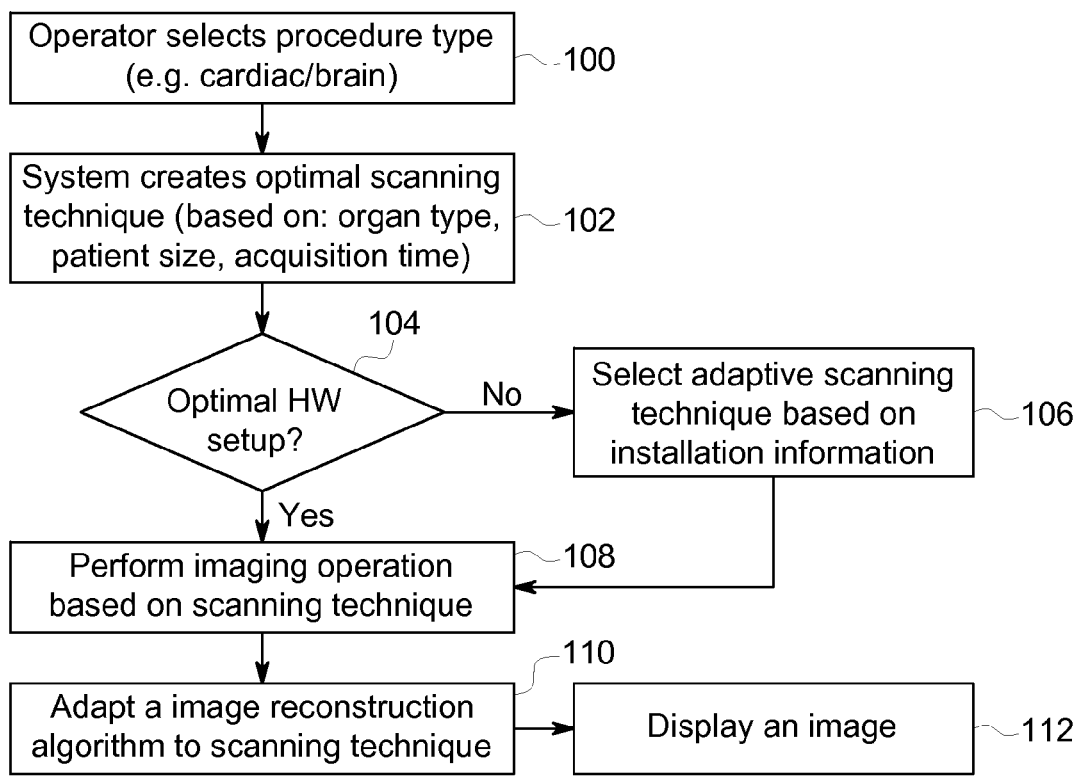
FIG. 7 is a flowchart of a scan operation, according to an embodiment.

FIG. 7 is a flowchart of a scan operation of the system, according to an embodiment. In step 100, the system operator gives a user input 39 indicating the procedure type, such as a brain scan, breast scan, thyroid scan, cardiac scan, or other object scan. This procedure type may also indicate whether the procedure is a single or multi-isotope imaging procedure.

In step 102, the system creates an optimal scanning technique of how the detector columns 22, detector heads 50, collimators 56, and detector elements 54 should be arranged. This optimal scanning technique can be based on organ type, patient size, desired acquisition time, for example. These can be user input values for each, or system detected values. For example, the patient size could be automatically determined by a quick scan of the environment. In another example, the system identifies which detector columns have high energy collimation and which have low energy collimation. Also, if some detector heads had both high and low energy collimation, this step will determine which detector heads should scan, in what direction the detectors should orbit, and in what order.

In step 104, the system determines if the hardware installed in the system can perform the optimal scanning technique. This can also be thought of as a determination if the optimal hardware setup is in place for the current situation based on installation information. If the system has all of the hardware installed for an optimal result (meaning the installation information matches the optimal scanning arrangement), the system proceeds to step 108. Otherwise, it proceeds to step 106.

If the system reaches step 106, the system has used the installation information to determine that the optimal scanning technique cannot be performed. This could be, for example, that one detector column is missing so the optimal arrangement cannot be accomplished and the scan time will necessarily be longer. It also could be, for example, that only some, but not all, of the detector heads have the capability to perform high energy collimation. In step 106, the system, using the installation information and/or other factors related to the scan type or scan object, creates a new adaptive scanning technique to meet the situation or retrieves a previously saved adaptive scanning technique from memory that can apply to the current situation. The adaptive scanning technique can add time to the scan, but can be lower cost because the operator or customer does have to pay for a fully populated or fully featured system. Optionally, the adaptive scanning technique may comprise gantry motion or rotation or both in order to bring an operating detector to a location where a missing or inoperative detector should have been.

In step 108, the system performs an imaging operation on the subject. The imaging operation is completed by controlling the hardware elements and collimators of the system in a manner fitting the selected scanning technique (either optimal or adaptive). This controlling can include, but is not limited to, extending or retracting detector columns 22, rotating detector heads 50 to different scan angles, or moving detector columns 22 around the gantry orbitally to a new radial angle to the subject.

In step 110, the system adapts a reconstruction algorithm based on an image acquisition scenario and reconstructs the imaging information picked up on detector elements 54 using imagine reconstruction module 34. The image reconstruction process or algorithm can be adapted to be more compatible with the selected scanning technique. This creates the highest quality image possible given the hardware constraints of the system.

In step 112, the system displays an image output to a user, operator, patient, or other party. This can be on display 40 or at some remote location after the image output has been transmitted over network 42. Alternatively, this could be saving the image to a memory device.

Figure 8:
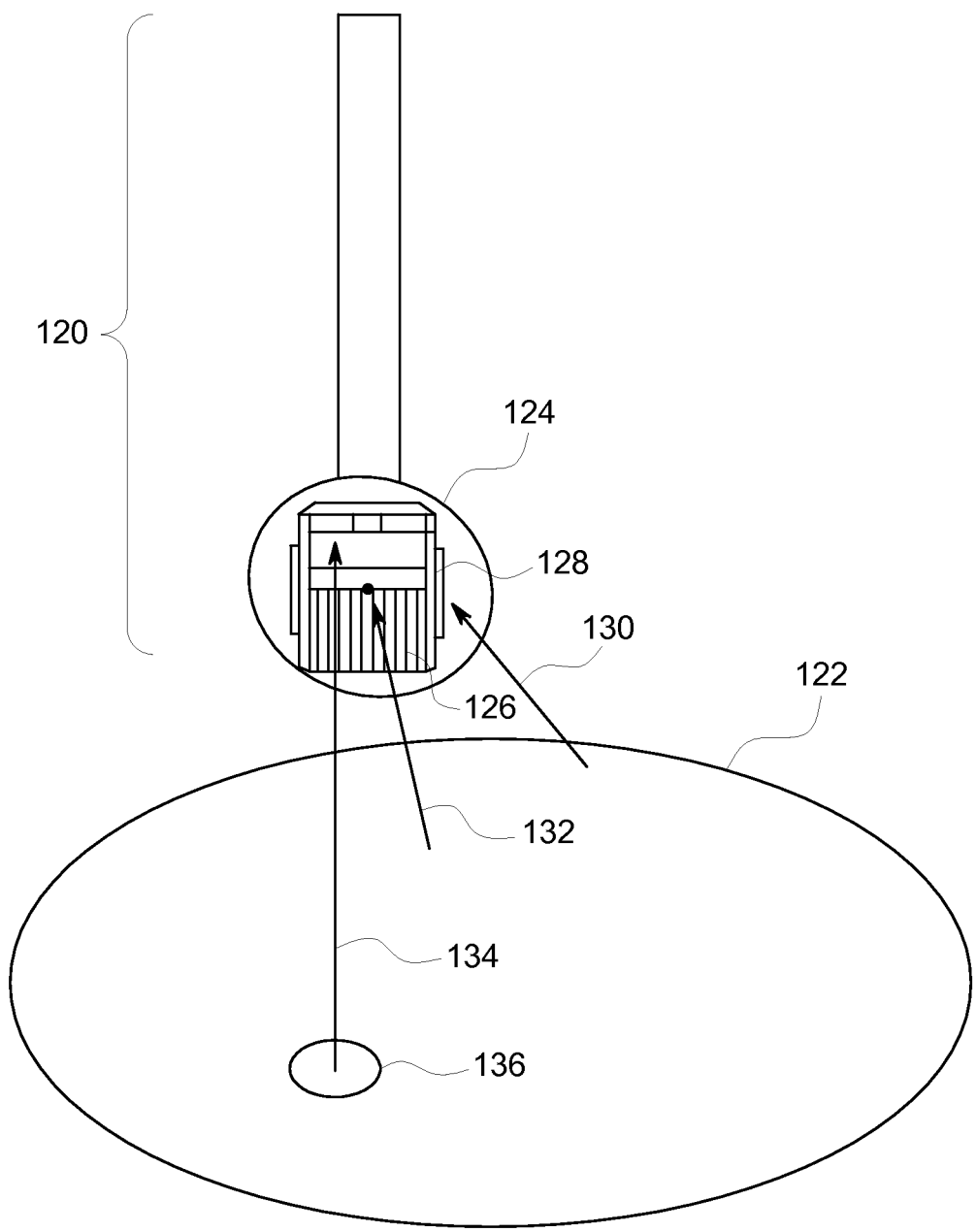
FIG. 8 is a view of a detector column during an imaging operation, according to an embodiment.

FIG. 8 is a view of a detector column during an imaging operation, according to an embodiment. Detector column 120 extends from a gantry towards patient 122. Patient 122 includes a radiopharmaceutical or radioisotope causing emission radiation to exit patient 122. Region of interest (ROI) 136 is, for example, an organ targeted in the medical imaging operation. Thus, detector head 124 has been moved radially towards ROI 136 and the head angle is pointed towards ROI 136. Detector head 124 includes parallel hole collimator 126. On both sides of detector head 124 are shields 128.

Shield radiation 130, collimator radiation 132, and ROI radiation 134 emit from patient 122. Shield radiation 130 does not reach the detector elements in detector head 124 because of shield 128. Blocking power of a shield is exponential with the effective thickness of the shield (the distance that the ray travels in the shield), thus in detector head 124 of FIG. 8, the effective thickness of shield 128 to shield radiation 130 is large. Collimator radiation 132 does not reach the detector elements in detector head 124 because collimator 126 blocks the emission angle of collimator radiation 132. ROI radiation 134 reaches detector elements in detector head 124 because of the proper angling of detector head 124 towards ROI 136. Both shield radiation 130 and collimator radiation 132 are blocked in this example due to the radiation energy levels not being strong enough to penetrate the blocking agents. Additional embodiments below address the problem where an emission radiation energy level is higher than can be blocked by a certain type of blocking agent.

Figure 9:
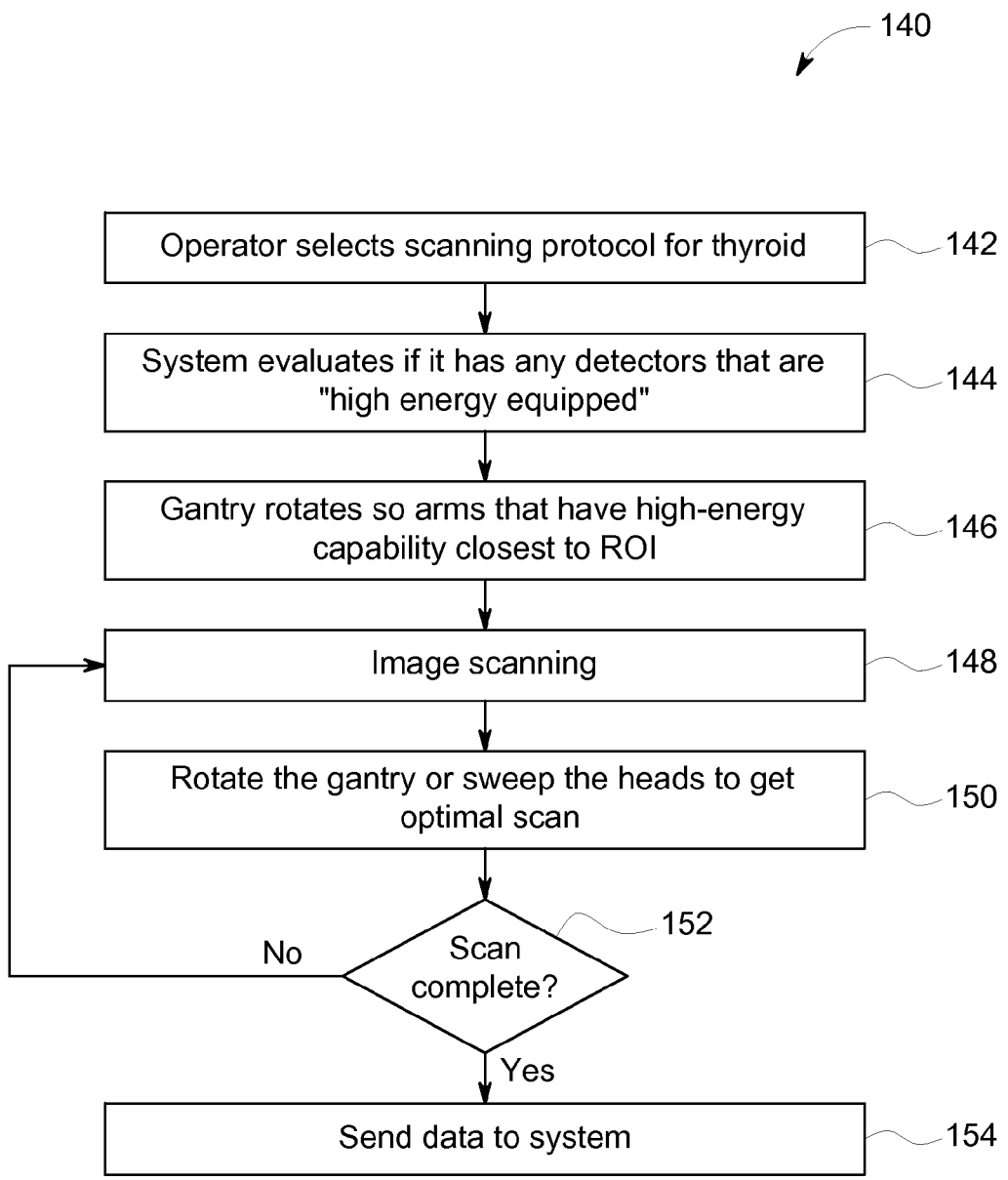
FIG. 9 is a flowchart for high energy imaging in a system that can perform both high and low energy imaging, according to an embodiment.

FIG. 9 is a flowchart for a high energy imaging method 140 in a system that can perform both high and low energy imaging, according to an embodiment. In this example, an operator selects a scanning protocol to scan the thyroid of a patient in step 142. A thyroid scan may include a high energy isotope and require high energy detection hardware.

In step 144, the system (using processor 32, for example) evaluates if any of the detector columns in the system are high energy equipped. High energy equipped means that the detector column includes a high energy collimator on some or all of its detector elements. A high energy equipped detector column may also have increased shielding on the sides of the detector head.

Figure 17:
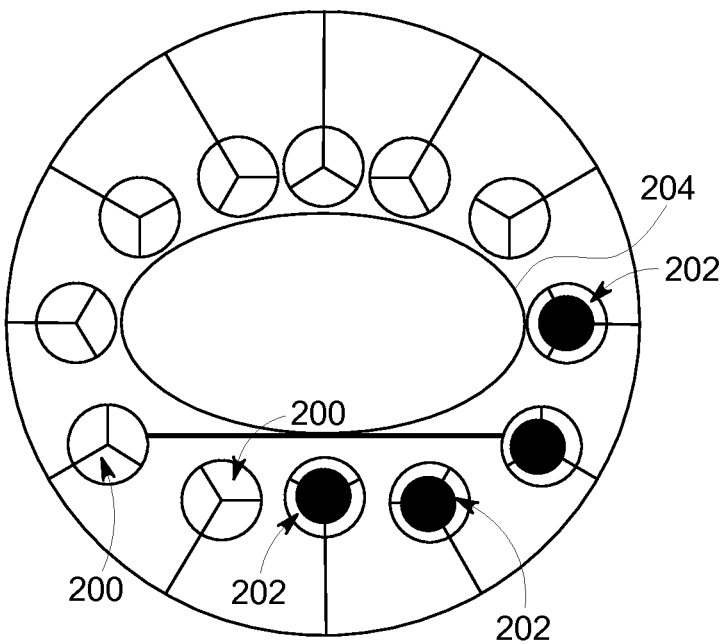
FIG. 17 is a front view of an imaging system with targeted high energy detector heads, according to an embodiment.

In step 146, the system instructs the gantry to rotate the detector arms, or detector columns, orbitally around the bore to a point where the most high energy equipped detector columns are close to the ROI, in this case, the thyroid of a patient. They system may also instruct the extension of the detector columns towards the ROI and the sweep angle of the detector heads to point towards the ROI. This may provide best image quality. FIG. 17 shows an example of this scenario.

In step 148, image scanning is performed, accepting emission radiation from the patient through the collimators to the detector elements on activated detector columns. In step 150, the system may rotate the gantry and/or sweep detector heads to get an optimal scan. In step 152, the system decides if the scan is complete. If YES, data is sent to the system, for example to image reconstruction module 34, in step 154. If NO, the system returns to step 148.

Figure 10:
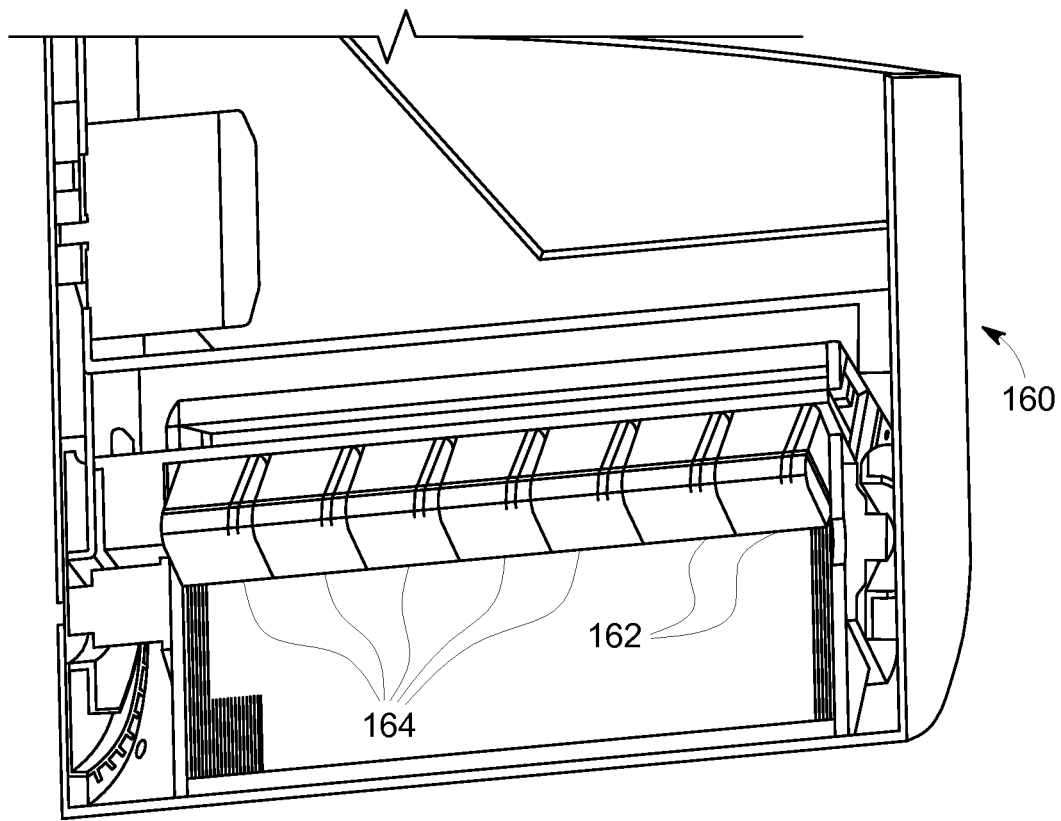
FIG. 10 is a detailed view of a detector head with varying collimator implementations, according to an embodiment.

FIG. 10 is a detailed view of a detector head with varying collimator implementations, according to an embodiment. Detector head 160 includes high energy detector elements 162 and low energy detector elements 164. High energy detector elements 162 include a pinhole or thick septa collimator. Low energy detector elements 164 include a thin septa collimator. High energy detector elements 162 may include detector materials specific to high energy emission detection. Low energy detector elements 164 may include detector materials specific to low energy emission detection. A detector head may have any number of detector element locations; seven is just an example in this embodiment. A detector head may have detector element locations with no detector element or collimator installed, as discussed further in the parent application incorporated herein by reference. Thus, as shown in FIG. 10, high energy detector elements 162 are towards one axial side of the detector head and low energy detector elements 164 are towards the other axial side of the detector head.

If all detector columns around the gantry are configured with such a detector head as in FIG. 10, then the system would form two axial rings of coverage. One high energy ring two elements wide, and one low energy ring five elements wide, in an embodiment. These would be along the X-Y, or scanning, axis. In a thyroid example, the ring two elements wide would include pinhole collimators.

Figure 11:
FIG. 11 is a side view of a detector element with associated thin septa collimator, according to an embodiment.

FIG. 11 is a side view of a detector element with associated thin septa collimator, according to an embodiment. Detector unit 170 is installed in a detector head of a detector column. Detector unit 170 can be a CZT detector unit in one embodiment. Detector unit 170 can be one detector element or a plurality of detector elements in varying embodiments. Detector elements can be aligned with the edges of the septa in one embodiment. Each detector element may include one or a plurality of pixels. Thin septa collimator 180 includes thin septa 172. Direct photon 174 is low energy photon. Due to its angle and position, direct photon 174 reaches detector element 170 for imaging. Low energy photon 176 is blocked by the thin septa and does not reach detector element 170.

High energy photon 178 hits and passes through thin septa 172 due to the thin width of the septa. High energy photon 178 thus hits detector element 170 and can cause misinformation in the image reconstruction process. In varying embodiments, a collimator can be connected, or attached to, to one or more detector elements.

Figure 12:
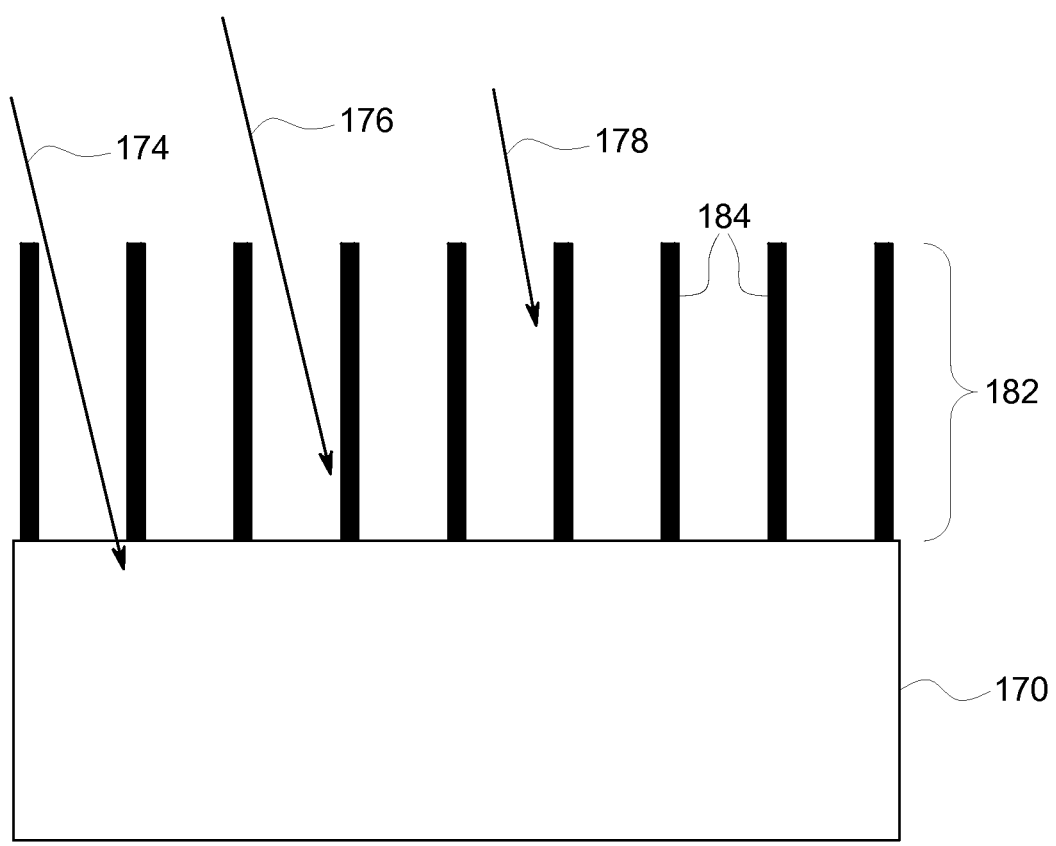
FIG. 12 is a side view of a detector element with associated thick septa collimator, according to an embodiment.

FIG. 12 is a side view of a detector element with associated thick septa collimator, according to an embodiment. Detector element 170 is installed in a detector head of a detector column. Thick septa collimator 182 includes thick septa 184. Direct photon 174 is low energy photon. Due to its angle, direct photon 174 reaches detector element 170 for imaging. Low energy photon 176 is blocked by the thick septa does not reach detector element 170. High energy photon 178 hits and is blocked by thick septa 184. Thus, a thick septa collimator can be better suited for high energy applications. Low energy images can be performed, but may have a reduced sensitivity due to the width of the septa.

Figure 13:
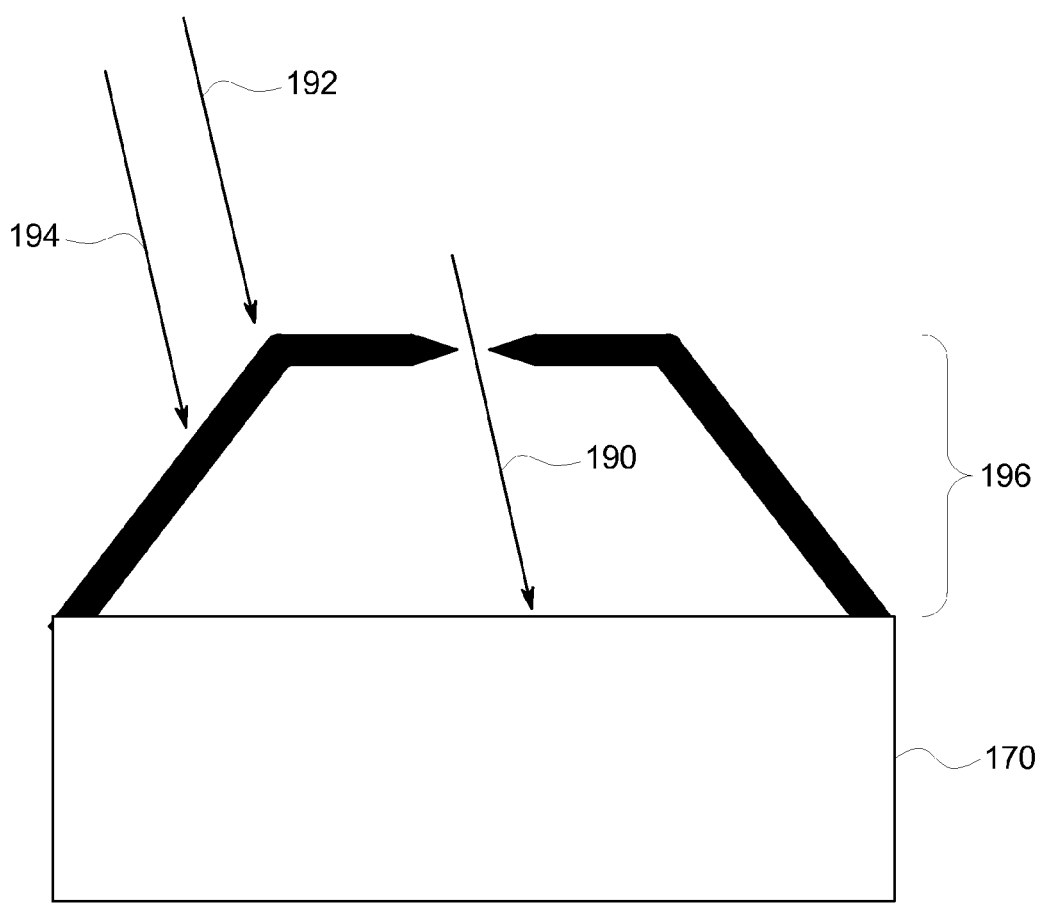
FIG. 13 is a side view of a detector element with associated pinhole collimator, according to an embodiment.

FIG. 13 is a side view of a detector element with associated pinhole collimator, according to an embodiment. Detector element 170 is installed in a detector head of a detector column. Pinhole collimator 196 allows pass-through of direct photon 190. Both high energy photon 194 and low energy photon 192 are blocked from reaching detector element 170 by pinhole collimator 196. Pinhole collimators may have lower sensitivity and/or lower resolution.

Figure 14:
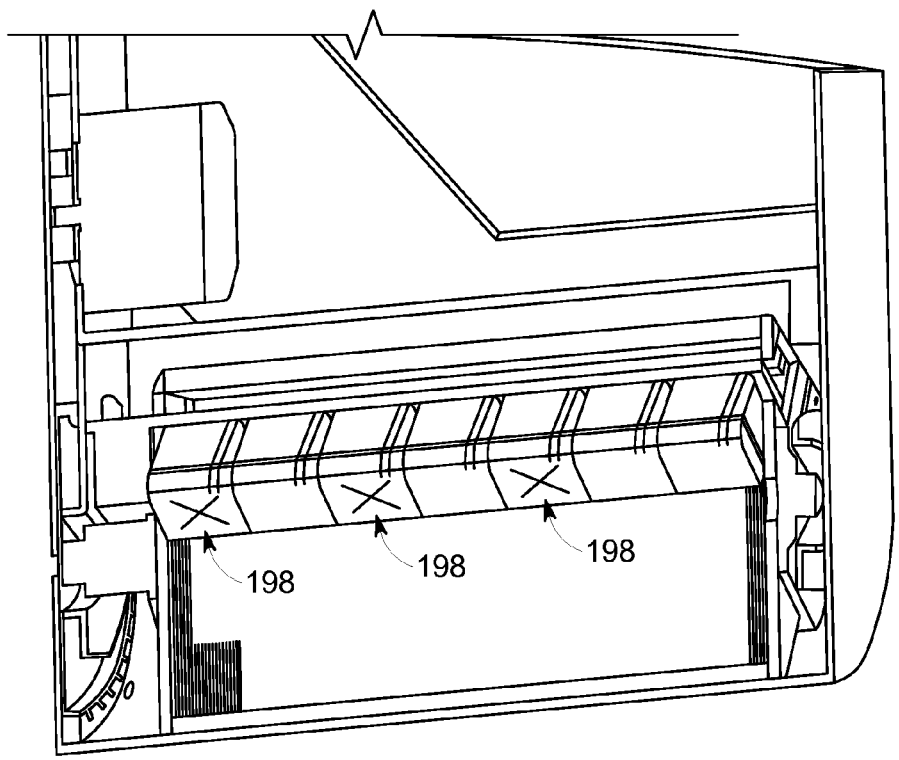
FIG. 14 is a detector head view of odd numbered detector columns, according to an embodiment.

FIG. 14 is a detector head view of odd numbered detector columns, according to an embodiment. In a system such as shown in FIG. 4, the odd numbered detector columns can have high energy collimators 198 (such as thick septa or pinhole) in slots detector element locations 1, 3, 5. The remaining elements can have low energy collimators.

Figure 15:
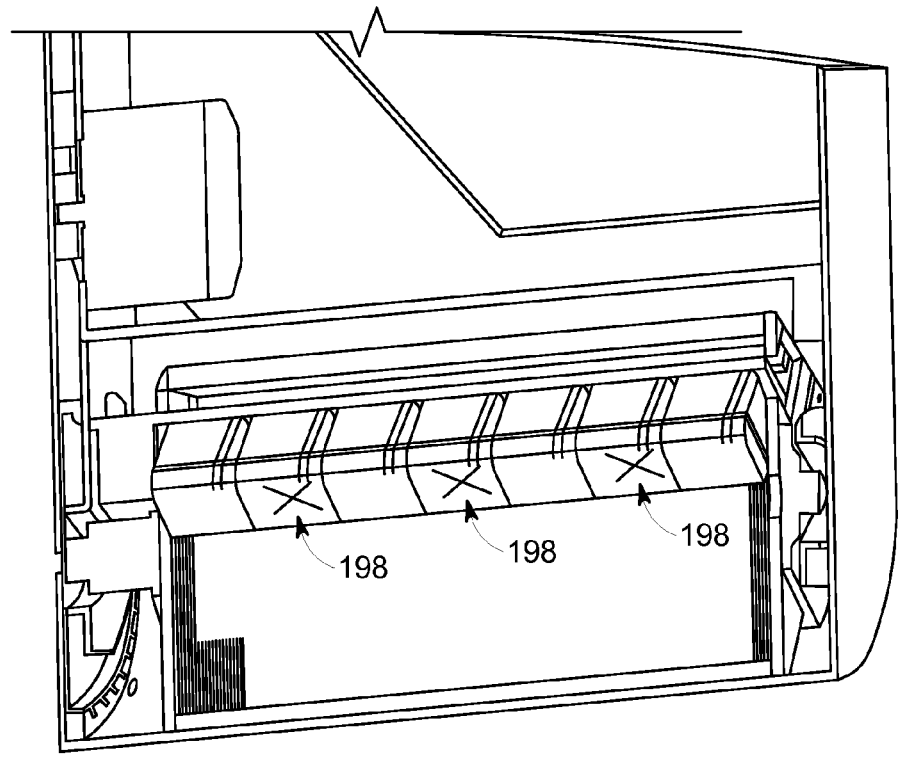
FIG. 15 is a detector head view of evened numbered detector columns, according to an embodiment.

FIG. 15 is a detector head view of even numbered detector columns, according to an embodiment. In a system such as shown in FIG. 4, the even numbered detector columns can have high energy collimators 198 (such as thick septa or pinhole) in slots detector element locations 2, 4, 6. The remaining elements can have low energy collimators. In an embodiment, some of the detector element locations can have no detector elements installed. The arrangement of FIG. 15 is a staggered arrangement, marked by an alternating pattern.

In a system of FIG. 4, where odd numbered detector heads are as shown in FIG. 14 and even numbered detector heads are as shown in FIG. 15, the system can effectively scan both high and low energy applications while still maintaining high quality images. This can support single and multi-isotope scanning. The system can rotate the detector columns around the patient so as to receive photons to each detector location with both an even and an odd detector column, best capturing both low and high energy photons simultaneously. This can save cost from having detector heads, and related collimators, that just perform one action or the other.

Figure 16:
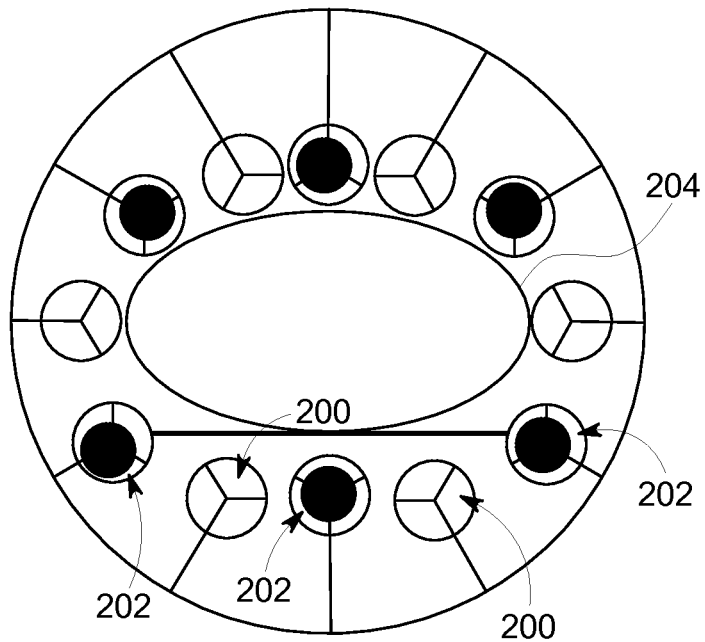
FIG. 16 is a front view of an imaging system with both high and low energy detector heads, according to an embodiment.

FIG. 16 is a front view of an imaging system with both high and low energy detector heads, according to an embodiment. High energy heads 202 have high energy collimators attached to all detector elements. Low energy heads 200 have low energy collimators attached to all detector elements. Thus, the system can collect both high and low energy emissions from patient 204 as the detector columns rotate orbitally around the bore.

FIG. 17 is a front view of an imaging system with targeted high energy detector heads, according to an embodiment. This embodiment is most suited to the flowchart of FIG. 9. This is because high energy heads 202 are all next to each other around the circumference of the bore. Thus, during a thyroid scan giving off high energy radiation, for example, the high energy heads can all move closest to the ROI in step 146.

Targeted organ scans can be performed well with the configuration of FIG. 17. Low energy heads 200 would not need to be extended towards the patient in such an embodiment where only high energy heads 202 would be activated. This saves electricity, wear, and cost on the system if only the certain heads needed are used for a given imaging operation.

Figure 18:
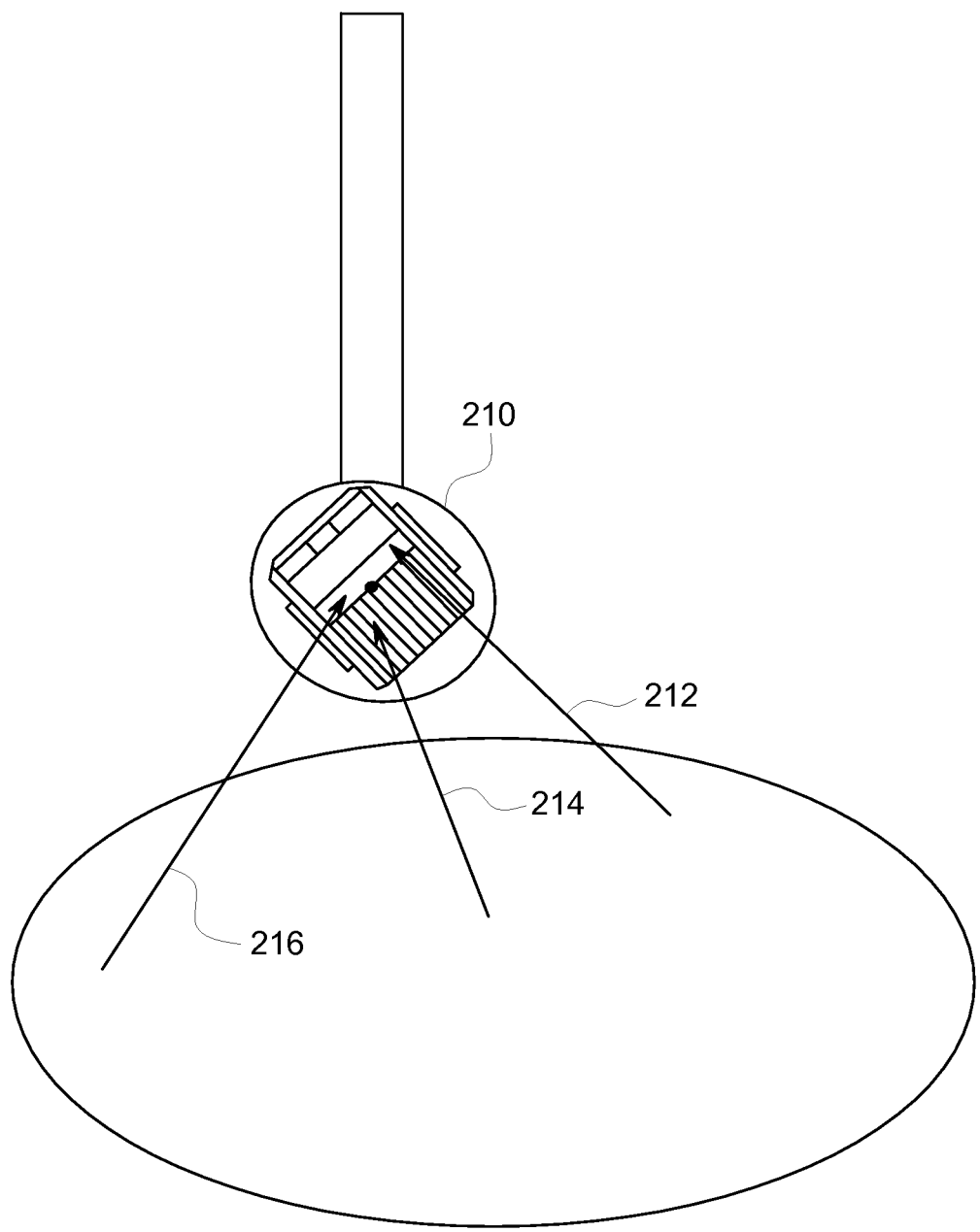
FIG. 18 is a view of a detector column with angled detector head during an imaging operation, according to an embodiment.

FIG. 18 is a view of a detector column with angled detector head during an imaging operation, according to an embodiment. Detector head 210 has been swiveled away from its angle in FIG. 8, as an example. Direct radiation 212 now passes through the collimator to the detector elements. Collimator radiation 214 is blocked by the collimator. Concentrated radiation 216 comprises too much radiation to be blocked by the shield on the side of the detector head in such an embodiment. This can be a concentration of low energy signals or a high energy signal. This can create problems as photons are received at the detector elements on one side of the detector head that should have not been allowed through.

Figure 19:
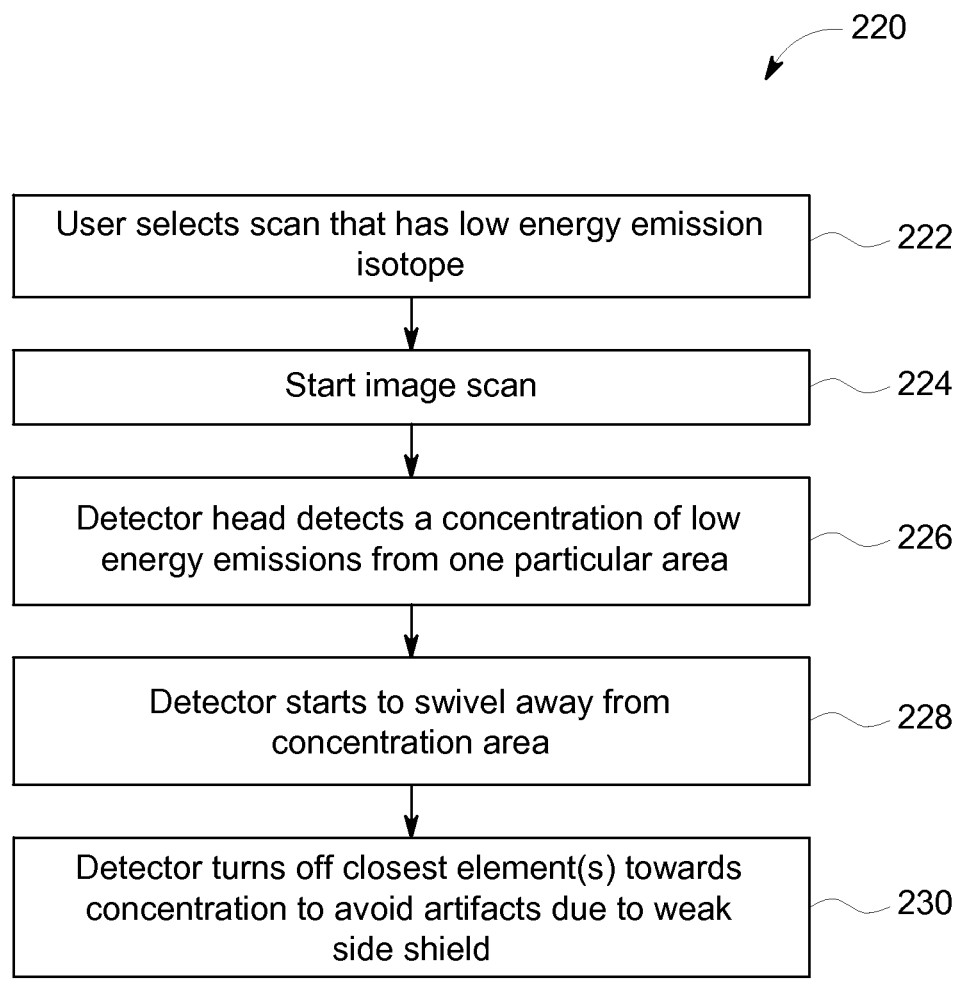
FIG. 19 is a flowchart detailing how a detector head may handle concentrated radiation from one angle, according to an embodiment.

FIG. 19 is a flowchart detailing how a detector head may handle concentrated radiation from one angle, according to an embodiment. The system can intelligently deactivate detector elements or detector element pixels where a concentration of emission data may make those detector elements unfit for best imaging. Sometimes, emission radiation is not uniform from the body of a patient due to how the radioisotope tracer has been distributed throughout the body. In addition, the concentration amounts can change over time in certain areas of the body. If a detector head sweeps away from the emission concentration area, the emissions may breach the detector head shield and hit the detector elements, as discussed above regarding FIG. 18.

In step 222 of process 220, a scan is selected for a patient. The scan may be selected by a user or operator, as shown in FIG. 19, or be selected by the system based on a set of criteria. In this example, a low energy emission isotope is used because the detector head may not have as strong of collimator or shielding. Thus, it is a good example to show this feature of the system.

In step 224, the system starts an image scan by detecting emission radiation photons on the detector elements of at least one detector head.

In step 226, the detector head, either in conjunction with a processor on the system or by its own processing circuitry, detects that a concentration of emissions are coming from one section of the patient. Multiple detector heads may also share information they receive about concentrations of tracer.

In step 228, the system detects that at least one detector head is swiveling or sweeping or angling away from an emission concentration. Thus, it triggers the error condition where the side shield on a detector head may not be strong enough for the concentration of emissions from that angle.

In step 230, the detector turns off the closest elements, typically one to three in a seven detector element configuration, to the concentration angle. Detector elements can have one pixel or multiple pixels. If a detector element has multiple pixels, step 230 can turn off one or more of the pixels instead of the whole detector element. For example, if looking at FIG. 18, one to three detector elements closest to the penetration of concentration radiation 216 would be deactivated. A criterion to determine one, two, or three detector elements for deactivating can be the amount of concentration of the tracer in the patient. This detector element deactivation would only last during the part of the image scan where the detector head angle is such that the concentration radiation may breach the side shielding. This detector element deactivation can prevent artifacts and other issues during image reconstruction due to tracer photons hitting detector elements that are not an intended part of the image scan. If the detector element deactivation cannot occur for some reason, the system can attempt to remove such artifacts during software image reconstruction.

Embodiments herein disclosed allow advanced diagnostic imaging applications to be performed. The system can handle both high and low energy radiation in a single imaging operation. An isotope that can produce low energy radiation may be technetium. An isotope that can produce high energy radiation may be iodine. The system can be configured in a variety of ways, with each detector head having a different configuration of collimators and shielding. The system can use the configuration information, or installation information, to perform intelligent decision making for fast and high quality imaging.

Thus, the system can be a nuclear camera system having a plurality of detector units, each detector unit having a field of view smaller than the width of a patient, wherein each detector unit comprises at least one collimator; at least one solid state pixelated detector, coupled to said at least one collimator; and a swiveling mechanism, to pivot said detector units to view a patient from a plurality of views, wherein at least one of said plurality of detector units has a low energy collimator, and wherein at least another one of said plurality of detector units has a high energy collimator.

Thus, the system can perform a method of operating a nuclear camera system for imaging high energy isotope comprising: swiveling a detector unit to view a section of said patient and selectively disabling at least one row of pixels near at least one edge of said at least one of pixelated detector module. The disabling can occur if the rate of radiation events on at least one pixel in said at least one row of pixels near at least one edge of said at least one of pixelated detector module is above a preset threshold.

As contemplated, the various embodiments provide a lower cost, upgradable, and customizable system for imaging operations. The configurable and controllable system of some embodiments could be controlled by user input. Thus, the user can override the automatic operation of the system and take full specific control of components of the system through a user interface.

This system, in some embodiments, can be considered a modular system. A non-technical operator can be one who has not had specialized or advanced training on the installation and adjustment of the imaging system. A technical operator could be a field engineer, for example.

The various embodiments and/or components, for example, the modules, or components and controllers therein, also may be implemented as part of one or more computers or processors. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a flash memory disk drive, optical disk drive, and the like. The storage device may also be other similar means for loading computer programs or other instructions into the computer or processor. As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An imaging system, comprising:
a gantry;
a plurality of imaging detector columns attached to the gantry;
a plurality of detector elements installed in each detector column, the plurality of detector columns further comprising shielding elements attached to at least two sides of a detector column to prevent radiation from reaching said detector elements from a side angle;
wherein, if a detector column detects received radiation from a side comprising a shield element, the system disables at least one detector element near to said side of the detector column; and wherein, for at least one detector column, a first portion of the plurality of detector elements are each attached to a low energy collimator; and a second portion of the plurality of detector elements are each attached to a high energy collimator.

2. The imaging system of claim 1, wherein:
at least one of the plurality of detector columns are configured to acquire Single Photon Emission Computed Tomography (SPECT) data.

3. The imaging system of claim 1, wherein:
the low energy collimator is a thin-septa collimator.

4. The imaging system of claim 1, wherein:
the high energy collimator is a thick-septa collimator.

5. The imaging system of claim 1, wherein:
the high energy collimator is a pinhole collimator.

6. The imaging system of claim 1, wherein:
at least one detector column simultaneously detects emissions from multiple isotopes inside an imaging subject.

7. The imaging system of claim 1, wherein each detector column has the same configuration, such that:
the plurality of detector elements attached to a low energy collimator are adjacent to one another and set towards one axial side of the detector column;
and the remaining portion of the plurality of detector elements attached to a high energy collimator are adjacent to one another and set towards the opposite axial side of the detector column.

8. An imaging system, comprising:
a gantry;
a plurality of imaging detector columns attached to the gantry;
a plurality of detector elements installed in each detector column;
wherein, for at least one detector column, a portion of the plurality of detector elements are each attached to a low energy collimator and a remaining portion of the plurality of detector elements are each attached to a high energy collimator; and
a processing system configured to:
develop an image acquisition scenario based system installation information and a requested imaging operation to be performed by the plurality of detector columns;
configure a physical position of a least one detector column based on the developed image acquisition scenario;
acquire image information from at least one detector element;
reconstruct image information into medical images; and
send said medical images to a display screen or a computer memory.

9. The imaging system of claim 8, wherein:
at least one of the plurality of detector columns are configured to acquire Single Photon Emission Computed Tomography (SPECT) data.

10. The imaging system of claim 8, wherein:
the low energy collimator is a thin-septa collimator.

11. The imaging system of claim 8, wherein:
the high energy collimator is a thick-septa collimator.

12. The imaging system of claim 8, wherein:
at least one detector column simultaneously detects emissions from multiple isotopes inside an imaging subject.

13. An image detector unit, comprising: a detector head comprising a plurality of detector elements; an arm for connecting the detector head with a support structure; a sweep motor for altering an angle of the detector head; wherein, at least a portion of the plurality of detector elements are each attached to a low energy collimator and the remaining portion of the plurality of detector elements are each attached to a high energy collimator; and shielding elements attached to at least two sides of the detector head to prevent radiation from reaching said detector elements from a side angle; and wherein if a detector unit detects received radiation above a preset threshold from a side comprising a shield element, the detector unit disables at least one detector element near to said side of the detector unit.

14. The image detector unit of claim 13, wherein:
the detector elements are configured to acquire SPECT data simultaneously from multiple isotopes inside an imaging subject.

15. An image detector unit, comprising:
a detector head comprising a plurality of detector elements;
an arm for connecting the detector head with a support structure; wherein, at least a portion of the plurality of detector elements are each attached to a low energy collimator and the remaining portion of the plurality of detector elements are each attached to a high energy collimator; and
wherein the detector elements are arranged in a row; and detector elements attached to a high energy collimator and detector elements attached to a low energy collimator are positioned in a staggered manner.

16. An imaging system, comprising:
a gantry with a bore therethrough;
a plurality of image detectors attached to the gantry, extending inside the gantry bore;
wherein at least one image detector includes only high energy collimation and at least one image detector includes only low energy collimation;
an annular rotary member attached to the gantry, wherein the plurality of image detectors are attached to the rotary member such that rotary member rotation causes the image detectors to orbit around the center of the bore;
wherein if a high energy medical scan is initiated in the system, the rotary member rotates the at least one image detector with high energy collimation near to a region of interest; and
wherein if a low energy medical scan is initiated in the system, the rotary member rotates the at least one image detector with low energy collimation near to a region of interest.

17. The imaging system of claim 16, wherein:
the low energy collimation is thin-septa collimation; and
the high energy collimation is pinhole collimation.

18. An imaging method in a medical imaging system with a gantry and a plurality of image detectors, comprising:
determining installation information of the system, wherein installation information includes high energy collimator configuration and low energy collimator configuration for each image detector;
acquiring SPECT data simultaneously from a plurality of isotopes inside an imaging subject, wherein at least one isotope emits high energy radiation and at least one isotope emits low energy radiation;
adjusting, based on said installation information, a detector head angle of at least one image detector, continuing the data acquisition from another imaging angle.

19. The imaging method of claim 18, wherein:
each image detector includes a plurality of detector elements;
high energy collimator configuration information includes the specific detector elements, for each image detector, that are attached to a pinhole collimator or thick septa collimator; and
low energy collimator configuration information includes the specific detector elements, for each image detector, that are attached to a thin septa collimator.

20. The imaging method of claim 18, further comprising:
disabling at least one detector element pixel near to a side of the image detector if, after adjusting a detector head angle, the image detector detects received radiation above a preset threshold from said side of the image detector.

* * * * *